US011375880B2

United States Patent
Kiedrowski

(10) Patent No.: US 11,375,880 B2
(45) Date of Patent: Jul. 5, 2022

(54) RIGID ENDOSCOPE

(71) Applicant: OLYMPUS WINTER & IBE GMBH, Hamburg (DE)

(72) Inventor: Gregor Kiedrowski, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 241 days.

(21) Appl. No.: 16/306,639

(22) PCT Filed: Jun. 1, 2017

(86) PCT No.: PCT/EP2017/063335
§ 371 (c)(1),
(2) Date: Dec. 3, 2018

(87) PCT Pub. No.: WO2017/211686
PCT Pub. Date: Dec. 14, 2017

(65) Prior Publication Data
US 2019/0159658 A1    May 30, 2019

(30) Foreign Application Priority Data

Jun. 8, 2016  (DE) .......................... 102016006903.1

(51) Int. Cl.
*A61B 1/00* (2006.01)
*A61B 1/018* (2006.01)

(52) U.S. Cl.
CPC ...... *A61B 1/00126* (2013.01); *A61B 1/00167* (2013.01); *A61B 1/00195* (2013.01); *A61B 1/00154* (2013.01); *A61B 1/018* (2013.01)

(58) Field of Classification Search
CPC ............ A61B 1/00126; A61B 1/00167; A61B 1/00195; A61B 1/00154; A61B 1/018
(Continued)

(56) References Cited

U.S. PATENT DOCUMENTS 4,776,668 A    10/1988  Fujimoto
5,665,051 A *  9/1997  Quick ................ A61B 1/00165
                                                    600/161
(Continued)

FOREIGN PATENT DOCUMENTS

CN         1132469 A    10/1996
CN       102379679 A     3/2012
(Continued)

OTHER PUBLICATIONS

English translation of International Preliminary Report on Patentability dated Dec. 20, 2018 together with the Written Opinion received in related International Application No. PCT/EP2017/063335.
(Continued)

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

A rigid endoscope including: a shaft; a body disposed at a proximal end of the shaft, a fiber image guide mounted to move longitudinally within the shaft and body; a securing section for securing the fiber image guide, the securing section being positioned within the body; a sliding element mounted to move longitudinally within the body; and a protective sheath encasing the fiber image guide; wherein the fiber image guide is twisted, for image rotation, in a longitudinal portion corresponding to the protective sheath.

6 Claims, 2 Drawing Sheets

(58) Field of Classification Search
USPC .......................................................... 600/138
See application file for complete search history.

(56) References Cited

U.S. PATENT DOCUMENTS

| | | | |
|---|---|---|---|
| 6,048,307 A | 4/2000 | Grundl et al. | |
| 6,419,628 B1 | 7/2002 | Rudischhauser et al. | |
| 7,758,498 B2* | 7/2010 | Ross | A61B 1/00142 600/101 |
| 2005/0192479 A1* | 9/2005 | Forster | G02B 23/26 600/130 |
| 2006/0276691 A1* | 12/2006 | Forkey | A61B 1/00096 600/172 |
| 2012/0053416 A1 | 3/2012 | Shibuya | |
| 2015/0258307 A1* | 9/2015 | Osypka | A61M 25/0136 604/529 |
| 2018/0071030 A1* | 3/2018 | Wood | A61B 5/0062 |

FOREIGN PATENT DOCUMENTS

| | | |
|---|---|---|
| CN | 105105699 A | 12/2015 |
| DE | 4024677 A1 | 2/1992 |
| DE | 19713275 A1 | 10/1998 |
| DE | 102004009219 A1 | 9/2005 |
| JP | S62-73224 A | 4/1987 |
| JP | 62-142017 A | 6/1987 |
| JP | 2000-121962 A | 4/2000 |
| JP | 2000121962 A * | 4/2000 |

OTHER PUBLICATIONS

International Search Report dated Aug. 8, 2017 issued in PCT/EP2017/063335.

* cited by examiner

RIGID ENDOSCOPE

CROSS-REFERENCE TO RELATED APPLICATION

The present application is based upon and claims the benefit of priority from PCT/EP2017/063335 filed on Jun. 1, 2017, which claims benefit to DE 10 2016 006903.1 filed on Jun. 8, 2016, the entire contents of each of which are incorporated herein by reference.

BACKGROUND

Field

The present application relates generally to rigid endoscopes, and more specifically to rigid endoscopes having fiber image guides.

Prior Art

An endoscope is known from DE 10 2004 009 219 A1.

Rigid endoscopes have a rigid shaft tube, which can be elastically bent to various extents depending on diameter and length. They can therefore be equipped with rod lens optics, for which they are suitable due to their low flexibility.

However, generic rigid endoscopes with fiber image guides find application when very thin shafts are used, which have improved flexibility and in which rod lenses would be at risk of breakage. Such generic endoscopes can be uteroscopes, which, in urology, are advanced through the bladder into the ureter and even through it to the kidney. Due to the given anatomical conditions, shaft diameters of not more than 5 mm are required for shaft lengths of more than 400 mm.

The generic endoscopes with their completely bend-insensitive fiber image guide can be bent without risk, but have system-related disadvantages, such as, the varying thermal expansion of the fiber image guide and the surrounding shaft tube. Even the non-centric mounting of the fiber image guide in the shaft tube can lead to longitudinal displacements during bending, through which the precise alignment of the optical system is disturbed.

SUMMARY

The proximal end of the fiber image guide must be able to be displaced longitudinally for the reasons mentioned, but must be kept as precise as possible in order not to disturb the alignment of the optical system. The sliding element, which can be mounted very precisely longitudinally displaceable with conventional guide technology, is used for this purpose. The proximal end region of the fiber image guide is to be secured to it, whereby very high precision requirements must in turn be imposed on this attachment. The primary concern is to have a precise attachment without risk of damage to the sensitive glass fibers.

An object is therefore to improve the attachment of the fiber image guide in the sliding element in terms of precision and preservation of the fibers in the generic construction.

Accordingly, the longitudinal region of the fiber image guide is designated with its attachment section with which the fiber image guide is secured to the sliding element. An adhesion, for example, could be made here, with the great disadvantage that this attachment is not detachable and thus the fiber image guide cannot or only with great difficulty be dismantled. In attaching tasks of this kind, the designer also thinks of a clamp. One could, for example, provide plier-like jaws that grip the side of the fiber image guide. Here, however, there is immediately the great risk of damage to the fibers or the clamping forces are reduced to such an extent that there is a risk of slipping.

The present disclosure assumes that special fiber image guides exist which are designed image-rotating in one section, i.e. with twisted fibers. These special fiber image guides are also used on endoscopes to rotate the image. Thus, for example, an image rotation can be effected in a space-saving manner without having to provide an additional reversing lens. However, such twisting sections of the fiber image guide have the disadvantage of being very sensitive mechanically. They are therefore usually encased by a protective sheath, which keeps dangerous tensile and bending forces away from the sensitive fibers. This protective sheath can be used for another purpose, namely to clamp on the protective sheath with high forces without endangering the glass fibers.

A rotation lock can be provided on the sliding element, with which the rotational position of the sliding element during its longitudinal displacement and thus the image orientation remains ensured.

The fiber image guide can be guided in a longitudinal bore through the sliding element and secured there with clamping screws seated in transverse bores. Such a configuration makes it possible to achieve a preserving and yet firm clamping in confined spaces.

DETAILED DESCRIPTION

Figure 1:
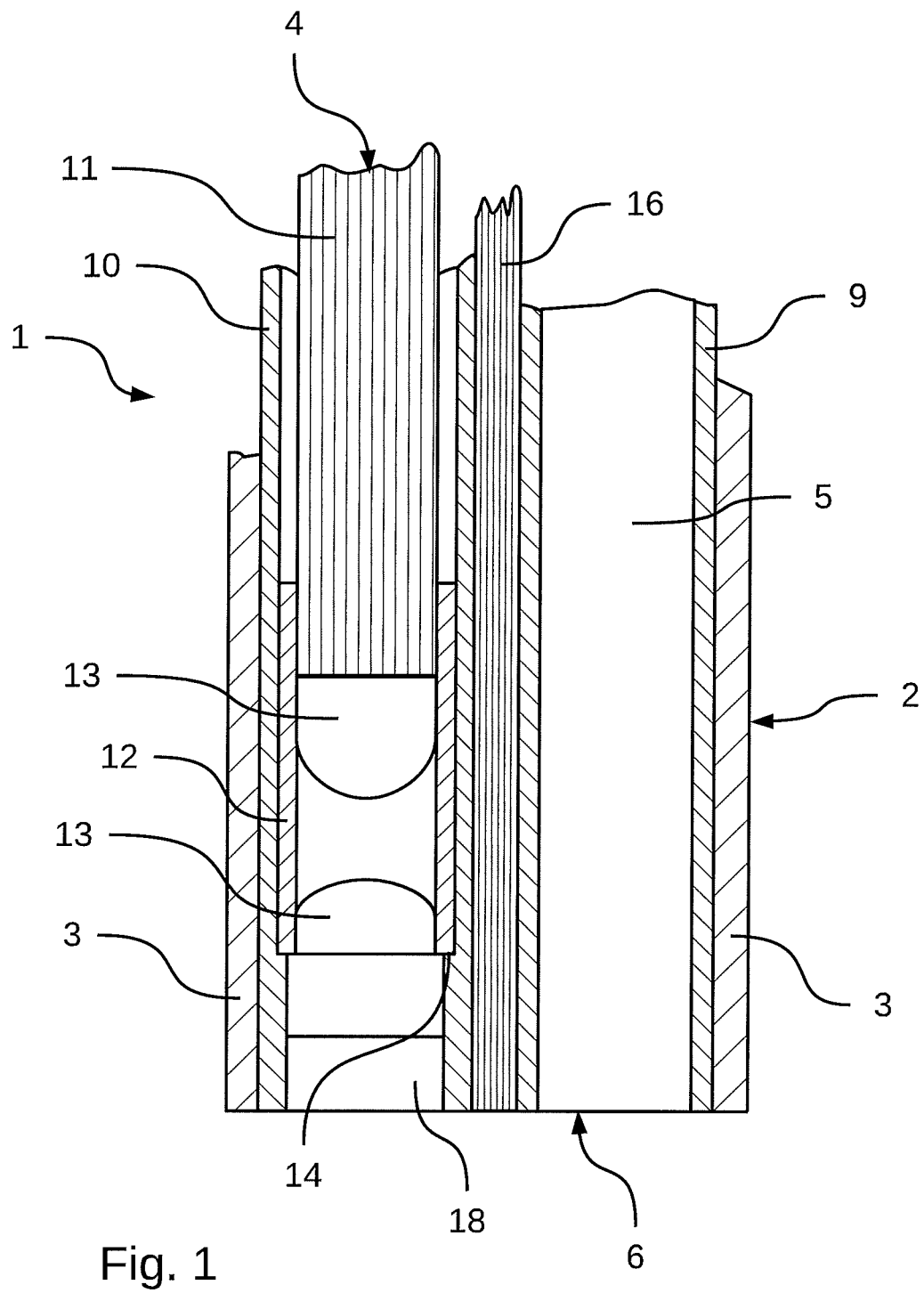
FIG. 1 illustrates a longitudinal section through a distal end region of the shaft of an endoscope.
Figure 2:
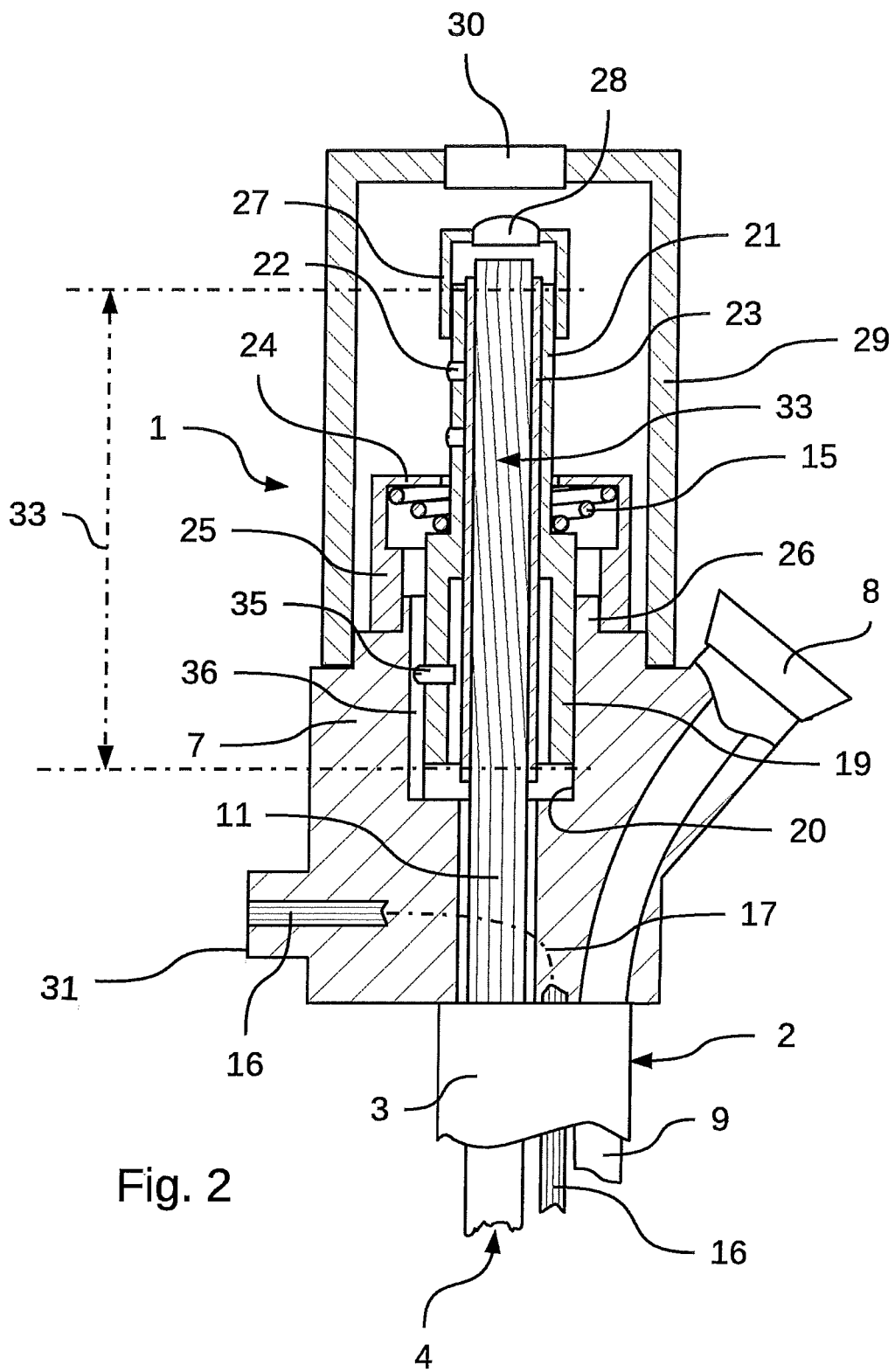
FIG. 2 illustrates a longitudinal section through a proximal end region of the shaft of FIG. 1

FIGS. 1 and 2 illustrate, in longitudinal sections, the two end regions of an endoscope 1, which is illustrated in the exemplary embodiment as a ureteroscope.

The illustrated endoscope 1 has an elongate shaft 2, which is formed from an outer shaft tube 3, in which an image guide 4 and a working channel 5 are arranged, which both extend from their distal end in an end face 6 of the shaft 2 into a main body 7 of the endoscope 1 adjoining the proximal end of the shaft 2. In this case, the image guide 4 passes through the main body 7 in a straight path, while the working channel 5 runs angled there to a diagonal side entrance 8 of the working channel 5.

Within the shaft tube 3, the working channel 5 is surrounded by a channel tube 9. In the illustrated embodiment, the image guide 4 runs over the entire length into a guide tube 10. A substantial component of the image guide 4 is a fiber image guide 11, which is held at its distal end in a lens tube 12 which carries the objective lenses 13.

The lens tube 12 is firmly connected, for example by adhesion, to the fiber image guide 11. The fiber image guide 11 and the lens tube 12 are, however, received longitudinally displaceably in the guide tube 10.

FIG. 1 shows the position of the fiber image guide 11, which is distally advanced as far as possible, with the lens tube 12, wherein the latter comes to a limit stop against a support 14 of the guide tube 10. The distal limit stop of the fiber image guide 11 illustrated in FIG. 1 is maintained in that it is advanced with a proximally arranged spring 15 in the distal direction to the support 14.

In the shaft tube 3, in addition to the image guide 4 and the working channel 5 in the remaining cross-sectional regions an optical fiber 16 consisting of glass fibers is laid, which, as illustrated in FIG. 2, runs through a schematically illustrated turning region 17 to a connecting piece 31 in the wall of the main body 7. From there, light can be coupled into the optical fiber 16 with an optical fiber connecting cable (not illustrated), which then emerges from the distal end face of the optical fiber 16 in the end face 6 of the shaft 2 in the observation region in front of the endoscope 1. This observation region is observed by the lens 13 through a window 18 located in the end face.

As shown in FIG. 2, the fiber image guide 11 passes through the main body 7 freely longitudinally displaceable. The proximal end region of the fiber image guide 11 is held in a sliding element 19, which is mounted in a cylinder region 20 of the main body 7 in the longitudinal direction of the fiber image guide 11.

The sliding element 19 carries a tube element 21, which is traversed by the fiber image guide 11 with a attachment section 33 located between the two dotted lines illustrated in FIG. 2. The attachment section designates the length range (i.e., the section) of the fiber image guide with which the fiber image guide is fastened or otherwise attached to the sliding element. It is a special fiber image guide, which, as illustrated in FIG. 2, is formed in the attachment section 33 with twisted fibers. In contrast, in the other longitudinal regions of the fiber image guide 11, the fibers run straight. They always transfer an image there while maintaining the angular position.

In contrast, the fibers in the attachment section 33 run twisted, specifically by 180° in the exemplary embodiment. The image is thus turned upside down in this region. As a result, an optionally additionally required reversing lens can be utilized.

A certain structural weakness of the fiber structure exists in this attachment section 33 before, in compensation thereof, the fiber image guide 11 in the attachment section 33 is encased by a protective sheath 23. It is a metal tube, which is formed during its production from the fiber image guide 11 consisting of glass fibers and sits substantially more stable than a subsequently attached sheath.

For the production of the fiber image guide 11, therefore, such a fiber image guide is sought which for other reasons has an image-rotating section 33 and is encased there with the protective sheath 23 for its protection. In this case, the fiber image guide 11 is adapted so that the casing 23 is located in the region of the sliding element 19.

Arranged in transverse bores in the tube element 21 are set screws 22, with which the clamping of the protective sheath 23 against the sliding element 19 takes place.

When bending the shaft 2 or during thermal expansions, there will be displacements of the sliding element 19. These could lead to a twisting, which is disadvantageous to the image stability. In order to prevent such undesired twistings, a further set screw 35 is provided in a transverse bore in the sliding element 19, which runs with its outwardly projecting end in a longitudinal groove 36.

The spring 15 is designed as a helical spring, which is arranged circumferentially around the fiber image guide 11. In the exemplary embodiment, the spring 15 is conical. As can be seen in FIG. 2, it can be pressed flat into a plane without the turnings touching each other.

The spring 15 is arranged so that it engages the tube element 21 and rests with the narrower end side against the proximal end face of the sliding element 19. With its other end, it lies against the inwardly facing flange 24 of a screw ring formed as a swivel nut 25. This is secured on an annular projection 26 projecting in the proximal direction on the proximal end face of the main body 7, for example, by welding and adhesion or, in the illustrated exemplary embodiment, by a screw. The screwing has the advantage that the swivel nut 25 together with the spring 15 can be unscrewed from the endoscope. Then the sliding element 19 can be pulled off in the proximal direction. Thus, the fiber image guide 11 is pulled off in the proximal direction and can be replaced or serviced.

At the proximal end of the sliding element 19, a closure cap 27 is placed on the tube element 21 and secured by a screw, for example. In the closure cap 27 a lens 28 is arranged which serves as an ocular lens and which also protects the distal end face of the fiber image guide 11 against contamination.

The closure cap 27 may also be gas-tight and protect the fiber image guide 11 at the proximal end against moisture. An additional or sole contamination and steam protection can also be provided by an outer cap 29, which has a window 30 and which is also secured, for example, by a screw, similar to that of the swivel nut 25, to a further shoulder of the proximal end face of the main body 7.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

01 Endoscope
02 Shaft
03 Shaft tube
04 Image guide
05 Working channel
06 End face
07 Main body
08 Entrance
09 Channel tube
10 Guide tube
11 Fiber image guide
12 Lens tube
13 Objective lens
14 Support
15 Spring
16 Optical fiber
17 Bending region
18 Window
19 Sliding element
20 Cylinder region
21 Tube element
22 Set screw
23 Protective sheath
24 Flange
25 Swivel nut
26 Annular projection
27 Closure cap
28 Lens
29 Outer cap
30 Window 31 Connecting piece
33 Attachment section
35 Set screw
36 Longitudinal groove

The invention claimed is:

1. A rigid endoscope comprising:
a shaft;
a body disposed at a proximal end of the shaft,
a fiber image guide movably mounted in a longitudinal direction within the shaft and body;
a sliding element disposed in the body such that the sliding element is movably mounted in the longitudinal direction within the body, the sliding element being disposed over an outer surface of the fiber image guide in a longitudinal region of the fiber image guide; and
a protective sheath encasing the fiber image guide, the protective sheath being disposed in the body to be movable with the sliding element, the protective sheath being located in the longitudinal region of the fiber image guide to correspond to the sliding element such that the protective sheath is disposed between the fiber image guide and the sliding element;
wherein the fiber image guide is twisted, for image rotation, in the longitudinal region corresponding to the sliding element and to the protective sheath.

2. The rigid endoscope according to claim 1, wherein the sliding element is configured to move in a longitudinal direction without rotation.

3. The rigid endoscope according to claim 1, wherein the sliding element has a longitudinal bore, the sliding element being fastened to the protective sheath with clamping screws seated in a wall of the sliding element.

4. A method of using the rigid endoscope having the fiber image guide according to claim 1, the method comprising:
encasing the fiber image guide with the protective sheath in the longitudinal region; and
fixing the protective sheath in an axial direction.

5. The rigid endoscope according to claim 1, wherein the fiber image guide and protective sheath run through a tube element of the sliding element.

6. The rigid endoscope according to claim 1, wherein the protective sheath is configured as a metal tube.

* * * * *